United States Patent
Izadyar et al.

(10) Patent No.: US 9,629,357 B2
(45) Date of Patent: Apr. 25, 2017

(54) CRYOPRESERVATION OF CELLS AND TISSUE FOR CLINICAL APPLICATION

(71) Applicant: PrimeGen Biotech LLC, Irvine, CA (US)

(72) Inventors: Fariborz Izadyar, Irvine, CA (US);
Jason Pacchiarotti, Irvine, CA (US);
Marnie Olmstead, Irvine, CA (US);
Kyle Howerton, Irvine, CA (US);
Thomas Ramos, Irvine, CA (US)

(73) Assignee: PrimeGen Biotech LLC, Santa Ana, CA (US)

( * ) Notice: Subject to any disclaimer, the term of this patent is extended or adjusted under 35 U.S.C. 154(b) by 515 days.

(21) Appl. No.: 14/171,055

(22) Filed: Feb. 3, 2014

(65) Prior Publication Data

US 2014/0220551 A1   Aug. 7, 2014

Related U.S. Application Data

(60) Provisional application No. 61/759,906, filed on Feb. 1, 2013.

(51) Int. Cl.
*A01N 1/00* (2006.01)
*A01N 1/02* (2006.01)

(52) U.S. Cl.
CPC ......... *A01N 1/0221* (2013.01); *A01N 1/0242* (2013.01); *A01N 1/0284* (2013.01)

(58) Field of Classification Search
None
See application file for complete search history.

(56) References Cited

U.S. PATENT DOCUMENTS

| | | | | |
|---|---|---|---|---|
| 5,004,681 A * | 4/1991 | Boyse | ................. | C12N 5/0647 424/529 |
| 5,192,553 A * | 3/1993 | Boyse | ................. | C12N 5/0647 424/529 |
| 5,788,963 A * | 8/1998 | Murphy | ............. | A61K 39/0011 424/185.1 |
| 6,140,121 A * | 10/2000 | Ellington | ............. | A01N 1/0221 435/366 |
| 6,194,137 B1 * | 2/2001 | Khirabadi | ................ | A01N 1/02 435/1.3 |
| 2007/0196811 A1 * | 8/2007 | Torres Simon | ...... | A01N 1/0221 435/1.3 |
| 2008/0064098 A1 * | 3/2008 | Allickson | ............ | C12N 5/0605 435/366 |

OTHER PUBLICATIONS

Methods in Molecular Biology, Cryopreservation and Freeze-Drying Protocols (2007)).*
Eilts, Theriogenology, 64:692-697 (2005).*
Terry et al., Liver Trans., 16:229-237 (2010).*
Critser et al., J. Reprod. Fert., 82:27-33 (1988).*
Baust et al., Organogen., 5:3, 90-96 (2009).*
Gee et al., J. Wildl. Mange., 49(2):480-484 (1985).*
Keros et al., Human Reprod., 20(6):1676-1678 (2005).*
Nsabimana et al., App. Env. Microbiol., 69(7):3826-3832 (2003).*
Pegg et al., J. Clin. Path., 12:477-482 (1959).*
Shu et al., Cytother., 12(2): 161-169 (2010).*
Thermo Scientific, Technical Manual (2009).*
Woelders et al., Cryobiol., 35:93-105 (1997).*
Woods et al., J. Hematother. Stem Cell Res., 9:161-173 (2000).*

* cited by examiner

*Primary Examiner* — Thomas J Visone
(74) *Attorney, Agent, or Firm* — K&L Gates LLP; Louis C. Cullman; Michelle Glasky Bergman

(57) ABSTRACT

Disclosed herein are methods for cryopreserving cells and tissues under clinical conditions, allowing production of viable cell products suitable for transplantation.

10 Claims, 3 Drawing Sheets

CRYOPRESERVATION OF CELLS AND TISSUE FOR CLINICAL APPLICATION

CROSS REFERENCE TO RELATED APPLICATIONS

This application claims the benefit under 35 USC §119(e) to U.S. Provisional Patent Application 61/759,906 filed Feb. 1, 2013, the entire contents of which are incorporated by reference herein.

FIELD OF THE INVENTION

The present application is directed to methods of cryopreservation of cells and tissue for transplantation back into the donor.

BACKGROUND OF THE INVENTION

Recent work in preservation of female fertility as well as new information on the nature of spermatogonial stem cells has prompted an investigation into the possibility of an effective clinical-grade procedure for the cryopreservation of cells and/or tissue.

Cryopreservation of reproductive cells and/or tissues has become an increasingly important methodology for fertility preservation. Success of autologous, cryopreserved ovarian tissue transplantation in patients has shown the ability of transplanted tissue to restore fertility in women and has generated live births. Currently, there are no methods for male patients that restore fertility or allow for future generation of new gametes in the event that their fertility is compromised due to testis damage. Cryopreservation of testicular cells and/or tissue prior to any fertility-compromising condition or therapy allows for future cell/tissue transplantation back to the autologous donor so that they regain the ability to naturally conceive their own biological children. Alternatively, these cells may be used to create new sperm outside the body through germ cell maturation protocols.

A procedure to preserve male fertility must be proven safe before it can be used in humans. Regulations and guidances set up by agencies such as the Food and Drug Administration (FDA) describe the procedures and systems that must be put into place before a product can be deemed safe to use in humans. Investigational techniques for cryopreserving testicular tissue and cells have been tested and reported by several groups; however, a clinical-grade protocol for the cryopreservation of human testicular cells or tissue has not been previously described. All previous studies used protocols non-compliant with current Good Tissue Practice (cGTP) standards, non-clinical-grade reagents, and/or animal products that made them unfit for clinical use. Additionally, no sterility testing was reported in these studies to ensure the absence of microbial contamination.

SUMMARY OF THE INVENTION

Disclosed herein is a clinically-applicable method for successfully cryopreserved human cells and tissue. For the first time, it was determined that testicular tissue and cells from patients undergoing sexual reassignment can be successfully cryopreserved and important cell populations can be enriched by the cryopreservation process. Sterility tests show that the cryopreserved cells and the thawed cells processed under cGTP and cGMP conditions were free from any microbial contamination. Therefore disclosed herein are methods of cryopreserving cells or tissue under controlled conditions.

Thus, disclosed herein is a method of clinical processing and cryopreservation of a cell-containing sample, the method comprising: obtaining a cell-containing tissue from an individual, optionally dissociating the tissue to form a single cell suspension; suspending the cells or tissue in a cryopreservation medium; placing the cryopreservation medium containing the cells or tissue in a cryopreservation vial; cooling the vial to 4° C. and holding the vial at 4° C. for a period of time; cooling the vial at a rate of −1° C. per minute to a temperature of −80° C.; cooling the vial at a rate of −50° C. per minute to a temperature of −120° C. to −160° C., holding the vial at −120° C. for a period of time between 0.1 and 60 minutes; and transferring the vial to the vapor phase of liquid nitrogen.

In another embodiment, the cryopreservation medium is a one-step cryopreservation medium and comprises phosphate buffered saline (PBS), human serum albumin (HSA), dextran, and dimethyl sulfoxide (DMSO). In another embodiment, the HSA is present at a concentration of between approximately 1% and approximately 20%, such as approximately 10%. In another embodiment, the dextran is present at a concentration of between approximately 0.1% and approximately 2%, such as approximately 1%. In another embodiment, the DMSO is present at a concentration of between approximately 1% and approximately 20%, such as approximately 10%.

In another embodiment, the vial is held at 4° C. for approximately 5-60 minutes, such as approximately 10 minutes. In yet another embodiment, the cooling step cools the vial to a temperature of approximately −130° C. to −150° C., such as approximately −140° C.

In one embodiment, the cryopreservation medium is added to the tissue or cells in a two step process comprising: suspending the cells or tissue in 0.5 volume of a first cryopreservation medium comprising HSA and PBS; and adding 0.5 volume of a second cryopreservation medium comprising PBS, dextran, and DMSO to the cells or tissue in the first cryopreservation medium, wherein the second cryopreservation medium is added drop wise over the course of approximately 0.5 to 10 minutes. In another embodiment, the second cryopreservation medium is added drop wise over the course of approximately 1 minute. In yet another embodiment, the first cryopreservation medium and the second cryopreservation medium are added to the cells or tissue by an automated syringe.

In another embodiment, the HSA is present in the first cryopreservation medium at a concentration of between approximately 2% and approximately 40%, such as approximately 20%. In another embodiment, the dextran is present in the second cryopreservation medium at a concentration of between approximately 0.1% and approximately 2%. In another embodiment, the DMSO is present in the second cryopreservation medium at a concentration of between approximately 1% and approximately 20%.

In another embodiment, a dissociated cell suspension is cryopreserved. In another embodiment, at least one tissue fragment is cryopreserved. In another embodiment, the cell-containing sample is a testicular sample. In another embodiment, the testicular sample is from a prepubertal male.

Further disclosed herein is a method of clinical processing of a cell-containing sample, the method comprising: obtaining and cryopreserving cells or tissue from an individual according to the method of claim 1; and thawing the cryopreserved cells or tissue in an automated thawing device.

DETAILED DESCRIPTION OF THE INVENTION

Figure 1:
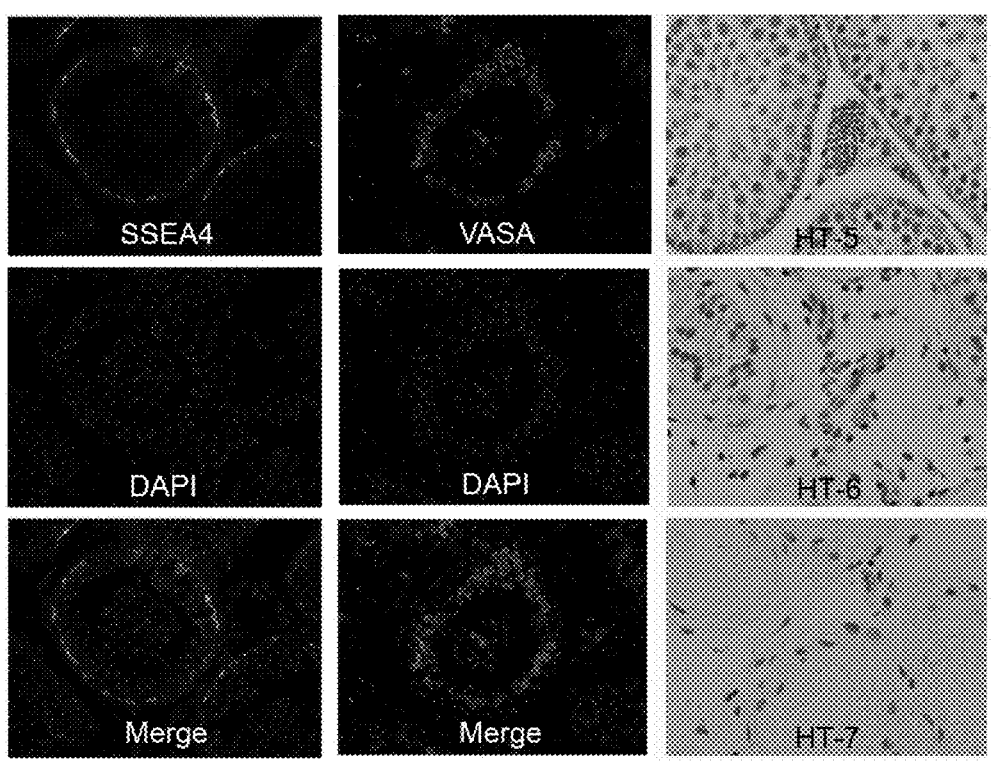
FIG. 1: Immunolocalization of cell marker and representative images of testicular cross sections from estrogen-treated patients. This figure shows localization of SSEA4 and VASA positive and various degree of spermatogenesis in the human testicular tissue collected from sexual reassignment patients. SSEA4 only stains the cells along the basement membrane of the seminiferous tubules. VASA stains all the germ cells including those along the basement membrane and in the lumen of the seminiferous tubules. Note various degrees of spermatogenesis was found in testes collected from three sexual reassignment patients (HT-5, HT-6, HT-7).

Disclosed herein is a clinically-applicable method for successful cryopreservation of human cells and tissue.

Besides creating a clinically applicable procedure, disclosed herein is a direct comparison of the cryopreservation of cells isolated from fresh human tissue with the cryopreservation of whole pieces from the same tissue. Cryopreservation can induce production of ice crystals from the water inside the cells, which damages the cells' internal structure and cellular membrane—and leads to cell death. The cells and tissue in this study were cryopreserved in a medium using cryoprotectants to prevent ice crystals from forming, thus improving the ability of the cells to survive freezing and thawing. In one embodiment, the human cells or tissue are from reproductive organs such as testes or ovaries. In other embodiments, the cells or tissue are from prepubertal donors. In yet another embodiment, the cells or tissue are from prepubertal males.

Viability of the cells can be assessed and the phenotype of the cells can be determined. Where the cells or tissue are testicular cells or tissue, there are three markers that define three important populations of cells in the human testes. First, stage specific embryonic antigen 4 (SSEA4) has been shown in non-human primates and humans to be an effective spermatogonial stem cell (SSC) marker. In vivo, SSCs require the support of Sertoli and Leydig cells as they go through spermatogenesis. An effective marker to identify and investigate Leydig cells is the luteinizing hormone receptor (LHR), the second marker used. Finally, VASA (also known as DDX4), is a specific germ cell lineage intracellular marker. All of these cell types, in addition to many other cell types, comprise the heterogeneous mixture of testicular cells and are affected in contrasting ways by cryopreservation of testicular cells or tissue. Cells isolated from fresh tissue were compared to both the cryopreserved cell suspensions and cells isolated from the cryopreserved tissue.

The cryopreservation of testicular cells and/or tissues is of particular importance to patients for whom sperm freezing is not an option. Prepubertal patients undergoing radiation and/or chemotherapy are at risk for fertility loss due to the cytotoxic effects of those therapies on the germinal epithelium—where SSCs are located. The direct toxic effects of chemotherapy and radiation exposure on the gonads are generally dose-dependent and the long-term effects of chemotherapy on the testes have not been well characterized. The survival rate among children with cancer has improved over the past several years; close to 80% are expected to survive. Although there are no established options for prepubertal boys who are later found to be infertile, their preserved testicular cells or tissue can potentially be used to restore their fertility.

Another population for whom this process is beneficial is men who have begun the process of sexual reassignment. These patients undergo hormone treatment regimens, which last varying amounts of time, and have devastating effects on spermatogenesis in the testes. For this reason, it is usually difficult or impossible for these men to preserve sperm after a critical point in their treatments for use in assisted reproductive techniques. Without sperm, the only option for these men to preserve their fertility may be the preservation of their testicular cells or tissue. This cryopreserved material would then be used in germ cell maturation procedures to produce sperm for use in assisted reproductive techniques. For the first time, it was determined that testicular tissue and cells from patients undergoing sexual reassignment can be successfully cryopreserved—and important cell populations can be enriched by the cryopreservation process. Sterility tests show that the cryopreserved cells and the thawed cells processed under cGTP and cGMP conditions were free from any microbial contamination.

There are many considerations that go into determining if cryopreservation of cells or tissue is most appropriate. The quality of the cells that result from either cell or tissue freezing is important—as measured here by the viability and the number of cells isolated. For certain types of tissue, such as testicular tissue, it is important to determine both the total viable population and the survival/enrichment of the SSCs, Leydig cells, and germ cells. Other considerations are also taken into account: cryopreservation of tissue requires less time and effort, is less expensive, and requires less equipment. On the other hand, cryopreserving cells isolated from fresh tissue has its advantages. First, more information is known about the cells—such as the quality of the cells as explained above. Secondly, the process of isolation and cryopreserving the cells eliminates any contamination found in the transport solution before processing. Thirdly, it is much easier to perform quality control and stability testing on the cryopreserved cells. Finally, the cryopreserved cells can be tested for sterility. Sterility testing in particular takes several weeks to obtain results using the methods currently employed in CLIA-approved laboratories as indicated in this study. If tissue is cryopreserved the results of sterility would not be obtained until far after the cells would be isolated and transplanted back into the body. For these reasons, and in certain circumstances, cryopreservation of cells isolated from fresh tissue is favorable over cryopreservation of tissue pieces.

Finding a clinical-grade method for preservation of cells or tissue will allow cryopreserved biologics to be used for future regenerative medicine applications in humans. Without a validated procedure, regulatory agencies would not allow cells/tissues to be transplanted back into the patient's body. It is possible to effectively isolate and/or cryopreserve cells and/or tissues; however prior methods did not comply with cGTP or cGMP regulations or employ clinical-grade reagents/supplies or possess the rigorous documentation that would make the procedures permissible for a clinical study.

Cryopreserving tissue is one option for preserving cells using these clinical-grade cryopreservation procedures, especially regarding the viability of those cells. In general, cryopreserving adult tissue yields more cells after cryopreservation than cryopreserving cells. In testicular tissue, of particular interest are the SSCs, represented in this and other studies by SSEA4+ cells. These cells have the potential to be transplanted back into the body to restore fertility, to be terminally differentiated into sperm for assisted reproductive techniques, or to be differentiated into different cell types for other regenerative medicine applications. Cryopreservation of adult testicular tissue generates greater recovery of SSEA4+ cells than dissociated cells.

The same was true for the other cell population investigated from adult testicular tissue herein. Leydig cells are responsible for production of testosterone and maturation of SSCs into functional gametes. Cryopreserving both cells and tissue enriched the total cell population for cells positive for LHR (a Leydig cell marker) but when cryopreserving tissue, the LHR+ cells were even more enriched after cryopreservation and thawing. The fact that Leydig cells survive cryopreservation so effectively indicated that these cells perhaps are more resistant to cryodamage and could support the germ cells after cryopreservation. It has been shown that Leydig cells are more resistant to cryopreservation compared to spermatogenic cells. Among all cell types present in the adult testes, more differentiated spermatogenic cells, including spermatocytes, spermatids and spermatozoa, are the most abundant cell types in seminiferous tubules and perhaps the most susceptible to cryodamage. The majority of the VASA positive cells in the adult testes are advanced germ cells. Surprisingly, VASA positive cells were also enriched after cryopreservation. Similar to SSCs and Leydig cells, VASA positive cells were less susceptible to damage when they were cryopreserved as part of whole tissue. In general, all three cell types studies were better preserved when the adult tissue was frozen as compared to cryopreservation of cell suspensions.

Therefore, in certain embodiments, unfractionated tissue is cryopreserved. Optionally, cells are disassociated from the tissue and/or specific cell types are isolated from the cryopreserved tissue after thawing.

In other embodiments, cells are disassociated from the tissue prior to cryopreservation and cells in suspension are cryopreserved. Additionally specific cell types can be isolated from the cell suspensions before cryopreservation and specific cell types cryopreserved.

Specific cell types can be isolated from tissue, either before or after cryopreservation by digesting with at least one clinical grade enzyme including, but not limited to, collagenases (I, II, and mixtures thereof), neutral proteases, thermolysin, trypsin, chymotrypsin, and dispase. In one embodiment, the enzyme is a mixture of collagenases (I and II) and thermolysin marketed by Roche Applied Sciences as Liberase.

In other embodiments, specific cell populations are detected either before or after cryopreservation including, but not limited to, SSEA4+ cells, CD49f+ cells, VASA+ cells, LHR+ cells, and FSHR+ cells Isolated cells or unfractionated tissues are cryopreserved in a one-step cryopreservation medium comprising components including, but not limited to, phosphate buffered saline (PBS), human serum albumin (HSA), dextran, and dimethyl sulfoxide (DMSO). In certain embodiments, HSA is present in the one-step cryopreservation medium at a concentration (w/v) between approximately 1% and 20%, or between approximately 2% and 18%, between approximately 3% and 16%, between approximately 4% and 14%, between approximately 5% and 15%, between approximately 6% and 14%, between approximately 7% and 13%, between approximately 8% and 12%, between approximately 9% and 11%. Alternatively, the concentration of HSA is approximately 5%, approximately 6%, approximately 7%, approximately 8%, approximately 9%, approximately 10%, approximately 11%, approximately 12%, approximately 13%, approximately 14%, or approximately 15%.

In certain embodiments, dextran is present in the one-step cryopreservation medium at a concentration (w/v) between approximately 0.1% and 2%, or between approximately 0.2% and 1.8%, between approximately 0.3% and 1.6%, between approximately 0.4% and 1.4%, between approximately 0.5% and 1.5%, between approximately 0.6% and 1.4%, between approximately 0.7% and 1.3%, between approximately 0.8% and 1.2%, between approximately 0.9% and 1.1%. Alternatively, the concentration of dextran is approximately 0.5%, approximately 0.6%, approximately 0.7%, approximately 0.8%, approximately 0.9%, approximately 1.0%, approximately 1.1%, approximately 1.2%, approximately 1.3%, approximately 1.4%, or approximately 1.5%.

In certain embodiments, DMSO is present in the one-step cryopreservation medium at a concentration (w/v) between approximately 1% and 20%, or between approximately 2% and 18%, between approximately 3% and 16%, between approximately 4% and 14%, between approximately 5% and 15%, between approximately 6% and 14%, between approximately 7% and 13%, between approximately 8% and 12%, between approximately 9% and 11%. Alternatively, the concentration of DMSO is approximately 5%, approximately 6%, approximately 7%, approximately 8%, approximately 9%, approximately 10%, approximately 11%, approximately 12%, approximately 13%, approximately 14%, or approximately 15%.

In another embodiment, the cells or tissue are combined with the cryopreservation medium in a two-step process. In the two-step process, the cells or tissue are first suspended in 0.5 volume of a first cryopreservation medium. Then, to the mixture of first cryopreservation medium and cells or tissue is added a 0.5 volume of a second cryopreservation medium dropwise over a period of time between approximately 0.5 to 20 minutes such that the final volume of cryopreservation medium is 1 volume. The cells or tissue are then cooled as described herein. The first cryopreservation medium comprises PBS and HSA as disclosed herein and does not include dextran or DMSO. The second cryopreservation medium comprises PBS, dextran, and DMSO.

The first cryopreservation medium contains HSA at a concentration (w/v) between approximately 2% and 40%, or between approximately 4% and 36%, between approximately 6% and 32%, between approximately 8% and 28%, between approximately 10% and 30%, between approximately 12% and 28%, between approximately 14% and 26%, between approximately 16% and 24%, between approximately 18% and 22%. Alternatively, the concentration of HSA is approximately 10%, approximately 12%, approximately 14%, approximately 16%, approximately 18%, approximately 20%, approximately 22%, approximately 24%, approximately 26%, approximately 28%, or approximately 30%.

The second cryopreservation medium comprises dextran at a concentration (w/v) between approximately 0.1% and 2%, or between approximately 0.2% and 1.8%, between approximately 0.3% and 1.6%, between approximately 0.4% and 1.4%, between approximately 0.5% and 1.5%, between approximately 0.6% and 1.4%, between approximately 0.7% and 1.3%, between approximately 0.8% and 1.2%, between approximately 0.9% and 1.1%. Alternatively, the concentration of dextran is approximately 0.5%, approximately 0.6%, approximately 0.7%, approximately 0.8%, approximately 0.9%, approximately 1.0%, approximately 1.1%, approximately 1.2%, approximately 1.3%, approximately 1.4%, or approximately 1.5%.

The second cryopreservation medium further comprises DMSO at a concentration (w/v) between approximately 1% and 20%, or between approximately 2% and 18%, between approximately 3% and 16%, between approximately 4% and 14%, between approximately 5% and 15%, between approximately 6% and 14%, between approximately 7% and 13%, between approximately 8% and 12%, between approximately 9% and 11%. Alternatively, the concentration of DMSO is approximately 5%, approximately 6%, approximately 7%, approximately 8%, approximately 9%, approximately 10%, approximately 11%, approximately 12%, approximately 13%, approximately 14%, or approximately 15%.

For the purposes of the instant disclosure and the concentrations disclosed herein, the term "approximately" refers to a concentration within 10% of the stated value.

Isolated cells are cryopreserved at a concentration between approximately $1 \times 10^6$ and $10 \times 10^6$ cells per vial, between approximately $2 \times 10^6$ and $9 \times 10^6$ cells per vial, between approximately $2 \times 10^6$ and $8 \times 10^6$ cells per vial, between approximately $3 \times 10^6$ and $7 \times 10^6$ cells per vial, between approximately $3 \times 10^6$ and $6 \times 10^6$ cells per vial, and between approximately $3 \times 10^6$ and $5 \times 10^6$ cells per vial.

Alternatively, isolated cells are cryopreserved at a concentration of between approximately $1 \times 10^6$ and $10 \times 10^6$ cells/ml, between approximately $2 \times 10^6$ and $9 \times 10^6$ cells/ml, between approximately $2 \times 10^6$ and $8 \times 10^6$ cells/ml, between approximately $3 \times 10^6$ and $7 \times 10^6$ cells/ml, between approximately $3 \times 10^6$ and $6 \times 10^6$ cells/ml, and between approximately $3 \times 10^6$ and $5 \times 10^6$ cells/ml.

Isolated cells or unfractionated tissues are cryopreserved by a process comprising obtaining the tissue, optionally isolating cells from the tissue, suspending the cells or tissues in a cryopreservation medium, place the cryopreservation medium containing the cells or tissue in cryopreservation vial, cooling the vial to 4° C. for a period of time between approximately 5 and 60 minutes, cooling the vials at a rate of 1° C. per minute to a temperature of −80° C., cooling the vials at a rate of 50° C. per minute to a temperature of −120° C. to −160° C., holding the vials at −120° C. to −160° C. for a period of time between 0.1 and 60 minutes, and transferring the vials to the vapor phase of liquid nitrogen (approximately −188° C.).

In certain embodiments, the cells are held at 4° C. before cryopreservation for between approximately 5 and 60 minutes, for between approximately 7 and 40 minutes, for between approximately 8 and 30 minutes, for approximately 30 minutes, or approximately 10 minutes.

Cryopreserved isolated cells are thawed by a process comprising removing the vial(s) from the vapor phase of liquid nitrogen and approximately immediately placing the vial in a 37° C. water bath, gently agitating the vial in the water bath until only a small piece of frozen material remains in the vial, slowly diluting the contents of the vial with 4° C. thawing solution, centrifuging the diluted contents of the vial at 400xg for 5 minutes at 4° C., and resuspending the cells in cooled thawing solution.

Figure 3:
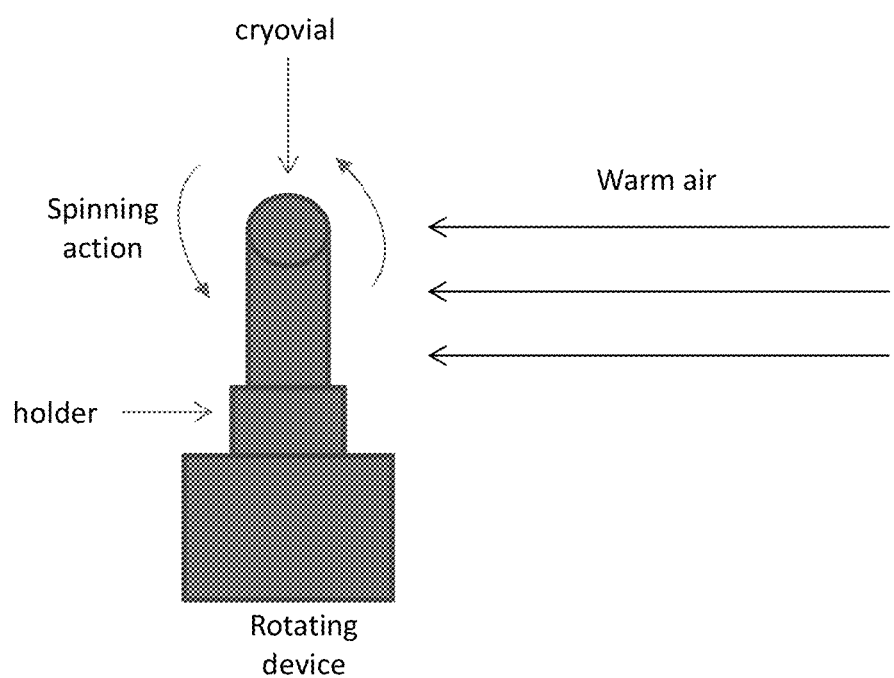
FIG. 3. Exemplary automated thawing device.

In one embodiment, to make the thawing procedure more compliant for clinical applications, the cells will be thawed in an automated thawing device (FIG. 3). The device contains a holder for cryovials containing the cells, wherein the holder is made of a thermo conductive material. The device is also equipped with a heater that blows warm air to the holder during the thawing process. The cryovial holder has heating element and rotates and agitates in different directions. The temperature of the cryovial holder, its speed and direction of the rotation and the time can be monitored automatically.

In one embodiment, a thawing solution comprises components including, but not limited to, PBS and HSA. In certain embodiments, HSA is present in the thawing solution at a concentration (w/v) between approximately 1% and 20%, or between approximately 2% and 18%, between approximately 3% and 16%, between approximately 4% and 14%, between approximately 5% and 15%, between approximately 6% and 14%, between approximately 7% and 13%, between approximately 8% and 12%, between approximately 9% and 11%. Alternatively, the concentration of HSA is approximately 5%, approximately 6%, approximately 7%, approximately 8%, approximately 9%, approximately 10%, approximately 11%, approximately 12%, approximately 13%, approximately 14%, or approximately 15%.

Alternatively, the cryopreserved isolated cells are thawed by a process comprising removing the vial(s) from the vapor phase of liquid nitrogen and approximately immediately placing the vial in a 37° C. water bath, gently agitating the vial in the water bath until only a small piece of frozen material remains in the vial, slowly diluting the contents of the vial with 4° C. thawing solution, centrifuging the cells and resuspending them in thawing solution.

In yet another embodiment, the cryopreserved tissue is thawed by a process comprising removing the vial(s) from the vapor phase of liquid nitrogen and approximately immediately placing the vial in a 37° C. water bath, gently agitating the vial in the water bath until the cryopreservation media is thawed, slowly diluting the contents of the vial with 4° C. thawing solution, holding the diluted contents at 4° C. for 5-10 minutes, and the tissue transferred to 4° C. PBS.

EXAMPLES

Materials and Methods cGTP and cGMP Environment. This study was performed under cGTP guidelines for a product regulated under section 361 of the Public Health Service Act and was compliant with other relevant FDA regulations and guidances at an FDA-registered and inspected tissue processing facility. All critical protocols were performed in a certified clean room. Moreover, protocols were performed using validated equipment and clinical-grade reagents and supplies according to cGMP guidelines. Documentation was followed for quality assurance/quality control and compliance with quality standards and regulations Tissue Collection and Testicular Cell Isolation. Sexual reassignment surgery (SRS) patients included in this study (5) were treated with hormones for a period of 6-12 months and their age varied between 25-40 years. All patients signed an informed consent form with the surgical facility agreeing for their tissue to be used for this study. Testicular tissue was also collected from deceased organ donors via the National Disease Research Interchange (NDRI) network. Testes from SRS patients were surgically removed from the scrotum and washed in sterile cGMP-grade phosphate buffered saline (PBS, Irvine Scientific) before being placed in a sterile bottle of 4° C. cGMP-grade PBS. After removal, the testes were shipped overnight in a validated shipper (ThermoSafe) between 2° C. to 8° C. and arrived approximately 24 hours after being removed from the patient. Testes from NDRI were surgically removed from the body, placed in PBS and shipped overnight on ice or cold gel-packs.

Upon arrival at the processing facility, the tissue was processed in the certified clean room. The seminiferous tubules were dissected by decapsulating the testes after removal of additional fat and membranes. The tissue was washed in cGMP-grade PBS. A piece of the tissue was cut off, weighed and placed in a sterile 50 mL conical tube with cGMP-grade PBS for cell isolation. Other pieces of tissue were cut, weighed, and used for tissue freezing (described below). Fresh or frozen/thawed tissue was dissected by sterile tweezers to smaller strips for enzymatic digestion with Liberase (Roche Applied Science), a cGMP-grade mixture of enzymes, was added to each piece for a final enzymatic digestion concentration of 0.3 units/mL of collagenase and 1000 units/mL of thermolysin. The tissue was digested at 37° C. on a reciprocating shaker at 110 RPM for 1.75 hours. Undigested tissue was removed from isolated cells by a sterile 100-μm cell strainer (BD Biosciences) before centrifuging the cells at 400×g for 5 minutes at 4° C. Cells were re-suspended in a mixture of cold cGMP-grade PBS and 10% human serum albumin (HSA, SeraCare Life Sciences) and kept at 4° C. for further processing.

Cell Count and Viability Assessment. Cells were counted on a validated hemacytometer with the addition of trypan blue (Life Technologies) to count the number of dead cells. Each sample was counted twice and an average was taken from the two counts. Viability was calculated by dividing the number of live (viable) cells by the total number of cells counted (live and dead) and displaying the number as a percentage where 100% represents a population of cells that is entirely alive and 0% represents a population that is entirely dead. In addition to trypan blue, viability of cells was confirmed using a flow cytometry based assay by 7AAD staining (see the flow cytometry analysis section). The number of cells obtained was normalized by the weight of the tissue and expressed as a ratio of viable cells per gram of tissue.

Cryopreservation. Freshly isolated cells were centrifuged as described above and re-suspended in cold cryopreservation media (CM) of 10% HSA, 10% DMSO/1% Dextran (Origen Biomedical), and cGMP-grade PBS. One mL of cell suspension, containing 3-5×10$^6$ cells, was pipetted into 1.8 mL cryovials (Nunc). Cells were cryopreserved by a validated Kryo-16 Controlled Rate Freezer (Planer). The protocol for the Kryo-16 was as follows: vials were held at 4° C. for 10 minutes before being cooled at a rate of −1° C./min to −80° C. The vials were further cooled at a rate of −50° C./min to −120° C. Vials were held at −120° C. until they were quickly transferred to a validated MVE TEC 3000 Dewar and stored in the vapor phase of liquid nitrogen at approximately −188° C.

Tissue pieces (120 to 500 mg) were cryopreserved in a similar manner. Tissue was placed in a cryovial with 1 mL of cold (4° C.) CM and held for 30 minutes at 4° C. prior to undergoing the cryopreservation procedure.

Flow Cytometry Analysis. Flow cytometry was conducted with a BD FACS Canto (BD) using unstained and secondary-antibody-only stained cells as controls. Cells from freshly isolated and thawed conditions were separately stained with Alexa-488 conjugated anti-human SSEA4 (Ebioscience), purified rabbit anti-human LHR (GeneTex), and purified rabbit anti-human VASA (Abcam). VASA is an intra-cellular protein, therefore the cells stained for VASA were first fixed in 4% paraformaldehyde (EMS) overnight and washed in PBS + 0.01% Triton-X. All primary antibody dilutions were optimized at 1:200 and staining time was for 30 minutes at 4° C. For stains that required a secondary antibody, cells were first blocked in 10% goat serum for 15 minutes and labeled with a goat anti-rabbit Alexa 488 antibody (Invitrogen) at 1:500 for 30 minutes at 4° C. All samples included 7AAD (BD Pharmingen) to determine and exclude the dead cells during analysis.

For each marker from each sample, the percentage of viable cells positive for that marker was determined. The percentage was then multiplied by the number of total viable cells isolated per gram of tissue to determine how many viable cells positive for each marker were isolated per gram of tissue. These numbers were compared between fresh tissue cell isolation and either cryopreserved cells or cryopreserved/thawed tissue to determine percent recovery of cells positive for each marker from each type of cryopreservation.

Cell and Tissue Thawing. Cryovials were removed from liquid nitrogen storage and immediately placed in a 37° C. water bath. Vials were swirled in the water bath until a small piece of frozen cells remained (~2 minutes). Thawed cells were transferred into a 50 mL conical tube and diluted with 9 mL of 4° C. cGMP-grade PBS and 10% HSA over the course of several minutes to dilute the CM 1:10. The cells were centrifuged as described above and re-suspended in PBS and 10% HSA for counting as described above. For thawing tissue, the tissue/CM was thawed and the CM was diluted as described above. Instead of centrifugation, the tubes of thawed tissue were held at 0-4° C. for 5-10 minutes to allow CM to dilute out of the tissue. Tissue was then transferred to PBS and placed on ice to await cell isolation. Cell isolation and counting was performed as described above.

Statistics. Average cell recovery was calculated by dividing the average number of cells after cryopreservation by the average number of cells isolated from fresh tissue. All other averages were calculated by dividing the summation of the values in the category by the sample size. Smith's Statistical Package was used for Two sample student T test for statistical analysis and P<0.05 was considered as significant. Standard error of the mean (SEM) was calculated by dividing the standard deviation by the square root of the sample size.

Sterility Testing. PBS used for transport of the tissue as well as samples of isolated and/or thawed cells for sterility testing were aseptically collected into sterile 1.8 mL cryovials. The vials were shipped to a qualified and CLIA-approved laboratory for sterility testing. Samples were inoculated into Trypticase Soy Broth and Fluid Thioglycollate Medium to test for the growth of yeast, fungi, aerobic and anaerobic bacteria. Cultures were grown for 14 days. Any detected growth after 14 days was a condition for failure of the sterility test.

Results

The viability of the cells is important for determining the effectiveness of the cryopreservation and the condition of the cells after freezing and thawing. The average viability of the cells isolated from fresh testicular tissue was 90.1%. When the same cells were cryopreserved and then thawed, the average viability dropped to 52.4%. When tissue from the same testes was cryopreserved, thawed, and the cells isolated by the same procedure as the fresh tissue, the average viability of the cells was 74.0%—lower than the average viability of cells isolated from fresh tissue by only 16.1% and higher than the average viability of the isolated cryopreserved cells by 21.6% (Table 1). The difference between the viabilities of the isolated cryopreserved cells and the cells from cryopreserved tissue was statistically significant (p=0.0019). This suggests that testicular cells have a better survival rate when frozen as tissue pieces as compared to freezing isolated cells.

TABLE 1

Viability of Cells Before and After Cryopreservation

| | Viability of Cells | | |
|---|---|---|---|
| Patient | Fresh Cells | Frozen Cells | Frozen Tissue |
| 1 | 84.9% | 38.1% | 70.1% |
| 2 | 91.9% | 64.1% | 81.8% |
| 3 | 93.0% | 53.8% | 68.9% |
| 4 | 90.6% | 53.3% | 75.9% |
| 5 | 90.2% | 52.8% | 73.5% |
| Average | 90.1% | 52.4%[a] | 74.0%[b] |
| SEM | 1.3% | 3.9% | 2.2% |

The viability of each cell population was determined by dividing the number of viable cells counted with the number of total cells counted (viable + dead). Two sample T test was used for statistical analysis and P < 0.05 was considered as significant.
[a,b] P = 0.0019.

When cells or tissue are cryopreserved and then thawed, some cells are naturally going to be lost due to cell damage and destruction. These lost cells are not accounted for when performing a simple live-dead count because they are only present as cellular debris. Therefore comparing just the viability is insufficient. A comparison was made between the number of viable cells initially cryopreserved and the number that remained after thawing. This test was utilized to determine if cryopreserving tissue pieces or cryopreserving isolated cells is a better method. The superior method should yield more viable cells recovered after cryopreservation and thawing. An average of $42.5 \times 10^6$ viable cells were isolated per gram of fresh testicular tissue. Upon thawing, an average of $14.0 \times 10^6$ of those cells were recovered—a recovery rate of 32.9%. When tissue pieces were cryopreserved, thawed, and enzymatically digested in the same manner as fresh tissue, the number of cells isolated per gram of tissue on average was 37.4% ($15.9 \times 10^6$ viable cells) of the number of cells isolated per gram of fresh tissue. This indicates that 4.5% additional cells may be recovered, on average, after cryopreservation of tissue pieces. However, this difference was not statistically significant (p=0.78), and it should be noted that only 3 out of the 5 patients showed greater recovery of cells when cryopreserving tissue. (Table 2).

TABLE 2

Number of Viable Cells Per Gram of Tissue and Recovery of Cryopreserved Cells

| | Viable Cells Per Gram of Tissue | | | Percent Recovery | |
|---|---|---|---|---|---|
| Patient | Fresh Cells | Frozen Cells | Frozen Tissue | Frozen Cells | Frozen Tissue |
| 1 | 15,300,000 | 4,057,018 | 6,630,259 | 26.5% | 43.3% |
| 2 | 42,800,000 | 13,312,147 | 32,958,482 | 31.1% | 77.0% |

TABLE 2-continued

Number of Viable Cells Per Gram of Tissue and Recovery of Cryopreserved Cells

| | Viable Cells Per Gram of Tissue | | | Percent Recovery | |
|---|---|---|---|---|---|
| Patient | Fresh Cells | Frozen Cells | Frozen Tissue | Frozen Cells | Frozen Tissue |
| 3 | 26,900,000 | 4,114,322 | 17,889,704 | 15.3% | 66.5% |
| 4 | 68,624,368 | 21,006,944 | 11,224,466 | 30.6% | 16.4% |
| 5 | 58,877,485 | 27,549,020 | 10,704,884 | 46.8% | 18.2% |
| Average | 42,500,371 | 14,007,890 | 15,881,559 | 33.0% | 37.4% |
| SEM | 9,313,258 | 4,390,103 | 4,390,059 | 4.8% | 11.7% |

The number of cells calculated per gram of tissue is compared between isolating cells from fresh tissue, from cryopreserved cells and cryopreserved tissue. For fresh cells, the weight of the tissue of each enzymatic digestion was determined. For frozen cells, the number of cells recovered from each frozen vial was used to calculate how many cells would have been recovered had the cells from 1 gram of tissue been frozen. For frozen tissue, the number of cells isolated from each piece after thawing was used in conjunction with the weight of the tissue before freezing. For all three, only viable cells were used for the calculations. Cell recovery was calculated by dividing the number of viable cells per gram of tissue from either the cryopreserved cell or cryopreserved tissue with the viable cells from fresh tissue cell isolation.

Immunolocalization of the cells positive for the specific markers used in this study is presented in FIG. 1. Testicular cell isolations are a mixture of the various component cells of the testes. Most importantly to fertility preservation are SSCs. The survival of these cells after cryopreservation is the key to fertility preservation or other therapeutic regenerative medicine techniques. The recovery and the percentage of the cells positive for each cell marker before and after cryopreservation are presented in Tables 3 and FIG. 2, respectively. For every gram of fresh tissue, on average 630,923 viable SSEA4+ cells were recovered. After cell thawing an average of 246,578 of those cells were recovered. This represented a recovery rate of 39.1%. By comparison, when tissue pieces were cryopreserved, thawed, and enzymatically digested, an average of 50.4% of the number of SSEA4+ cells isolated per gram of fresh tissue was recovered—higher by 11.3% (50.4%-39.1%) in absolute terms than when cryopreserving isolated cells. However, only 3 out of the 5 patients showed a higher recovery percentage when cryopreserving tissue rather than isolated cells. Although there is a trend that cryopreserving testicular tissue allows for more survival of the SSCs than cryopreserving isolated cells, the difference was not statistically significant (p=0.4254).

Interestingly, the recovery rate of SSEA4+ cells was higher than the recovery rate of the total cell population. For cryopreserved cells, the average recovery of SSEA4+ cells was higher by 9.0% in absolute terms. For cryopreserved tissue, recovery rate of SSEA4+ cells was higher by 6.1% in absolute terms compared with the average recovery of the total cell population. The difference in recovery of SSEA4+ cells between cryopreserving cells and cryopreserving tissue was not significant (p=0.14), although 4 out of 5 patients had higher recovery of SSEA4+ cells from cryopreserved tissue. The difference between the recovery of viable SSEA4+ cells isolated before and after cryopreservation of cells was not statistically significant (p=0.1484), as was the difference between fresh tissue isolation and frozen tissue isolation (p=0.5432). Even though cryopreservation leads to the loss of some SSEA4+ cells, it enriches the total population for SSEA4+ cells in the cell suspension.

TABLE 3

Recovery of Viable Cells Positive for Cell Marker Per Gram of Tissue

| | SSEA4+ | | | LHR+ | | | VASA+ | | |
|---|---|---|---|---|---|---|---|---|---|
| Patient | Fresh Cells | Frozen Cells | Frozen Tissue | Fresh Cells | Frozen Cells | Frozen Tissue | Fresh Cells | Frozen Cells | Frozen Tissue |
| 1 | 382,500 | 133,392 | 126,144 | 459,000 | 222,571 | 523,697 | 10,128,600 | 2,894,214 | 5,642,505 |
| 2 | 642,000 | 271,081 | 540,099 | 1,883,200 | 378,955 | 5,003,870 | 8,089,200 | 5,820,763 | 24,075,066 |
| 3 | 215,200 | 141,845 | 215,335 | 1,102,900 | 67,546 | 1,069,848 | 10,733,100 | 1,939,856 | 11,733,700 |
| 4 | 829,602 | 259,954 | 108,069 | 3,402,562 | 1,201,910 | 644,282 | 28,455,915 | 11,992,882 | 6,595,656 |
| 5 | 1,085,311 | 426,618 | 599,564 | 1,141,806 | 1,865,490 | 3,814,563 | 25,813,056 | 15,991,324 | 6,356,519 |
| Average | 630,923 | 246,578 | 317,842 | 1,597,894 | 747,294 | 2,211,252 | 16,643,974 | 7,727,808 | 10,880,689 |
| SEM | 146,814 | 50,549 | 99,337 | 477,708 | 323,267 | 872,536 | 4,096,440 | 2,567,434 | 3,288,223 |
| Percent Recovery | N/A | 39.1% | 50.4% | N/A | 46.8% | 138.4% | N/A | 46.4% | 65.4% |

The number of cells positive for each marker per gram of tissue isolated from fresh tissue cell isolation, and recovered from either frozen cell or frozen tissue. Percent Recovery was calculated by dividing the average after cryopreservation by the average before cryopreservation. No significant differences were observed.

Leydig cells produce testosterone and are important for the proper proliferation and differentiation of SSCs into functional gametes. As such, their survival could be important for post-cryopreservation maturation of SSCs. An average of 46.8% of Leydig cells as indicated by LHR was recovered after cryopreserving isolated cells. When cryopreserving tissue pieces, on average 138.4% of LHR+ cells were recovered—an indication that more LHR+ cells are able to be isolated by first cryopreserving the tissue than if the LHR+ cells were isolated from fresh tissue. Again, 4 out of the 5 patients had higher recovery of LHR+ cells from cryopreserving tissue compared with cryopreserving cells, although the results were not statistically significant (p=0.1225).

Similar to SSCs, as indicated by SSEA4, cryopreservation enriched the population of supporting Leydig (LHR+) cells in the total cell population. The average recovery of LHR+ cells in the cryopreserved cells was higher by 16.7% in absolute terms than the average recovery of the total cell population. The average number of LHR+ cells isolated from cryopreserved tissue was higher by 94.1% in absolute terms than the recovery of the total cell population from the same tissue. Both cryopreserved cells and tissue had a higher rate of recovery of LHR+ cells than total cell population in 3 out of the 5 patients while at the same time neither enrichment was statistically significant (p=0.4136 and p=0.0743, respectively). The results suggest that LHR+ cells are enriched by both tissue and cell cryopreservation.

VASA is an intra-cellular transcription factor expressed in all germ cells and was used as an indicator of the survival of the total germ cell population during cryopreservation. Thawed cells isolated from fresh tissue, on average contained 46.4% of the VASA+ cells that were cryopreserved. When tissue was cryopreserved, the number of VASA+ cells isolated per gram of tissue was on average of 65.4% compared with the number of VASA+ cells isolated per gram of fresh tissue. In 3 out of 5 patients, more VASA+ cells were recovered from cryopreserving tissue and in the other two cryopreserving cells preserved more VASA+ cells. However, the greater number of VASA+ cells recovered after tissue cryopreservation was not statistically different from cryopreservation of cells (p=0.0731).

Figure 2:
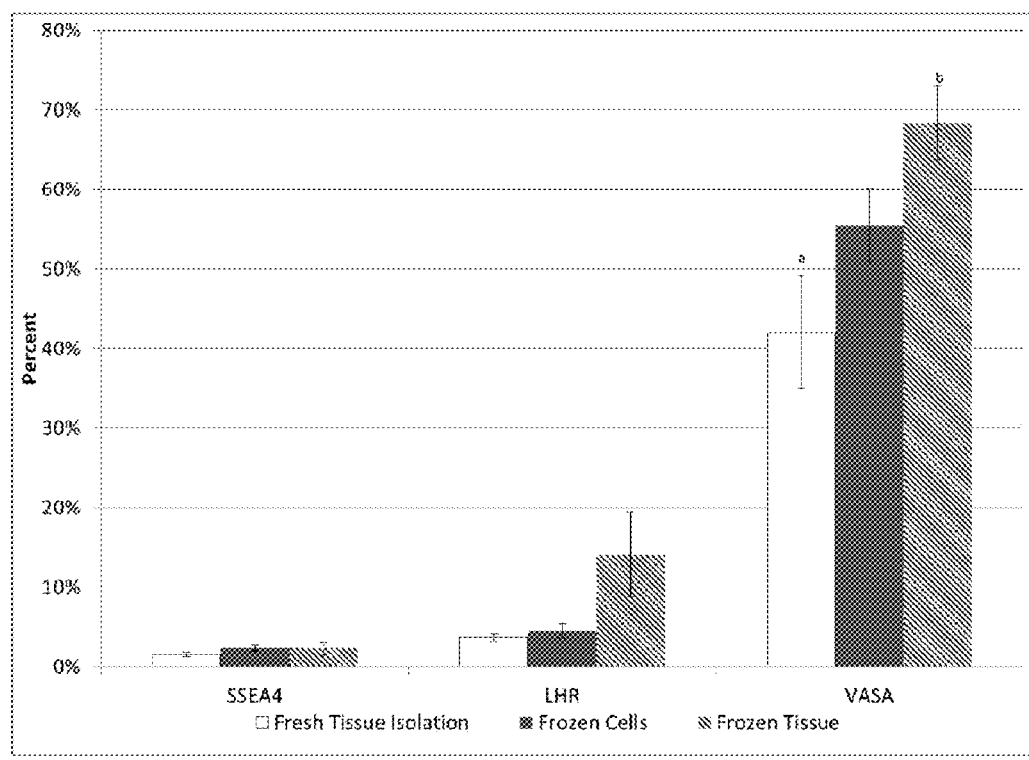
FIG. 2: Flow cytometry analysis of the enrichment of cells positive for each marker before and after cryopreservation. The numbers of viable cells positive for each marker were determined by flow cytometric analysis and are expressed as a percentage of the total viable cells in each condition. VASA positive cells were fixed before staining. VASA positive cells were counted without information about which ones were viable or dead. This graph shows that the average percentage of cells positive for each marker is higher after cryopreservation of cells and tissue. Two sample T test was used for statistical analysis and $P<0.05$ was considered as significant. ab: $P=0.0188$.

VASA+ cells were enriched when cryopreserving either cells or tissue. For cryopreserved cells, the average recovery rate of the VASA+ cells was higher by 16.3% in absolute terms than the average recovery rate of the total cell population. Similarly, for cryopreserved tissue, the average number of VASA+ cells isolated per gram of tissue was enhanced by 21.1% in absolute terms. Neither enrichment was statistically significant (p=0.2334 and p=0.3052, respectively) (FIG. 2).

To ensure that there was no contamination of either the cells/tissue or the processing environment, sterility testing was performed on the tissue transport PBS, on the cryopreserved cells, the thawed cells, and the air and surfaces in the clean room. For 3 out of the 5 patients, PBS and cells were sent to a CLIA-approved and FDA-registered clinical microbiology laboratory. Each sample of PBS used to transport the tissue was found to be contaminated with several microorganisms. This was likely due to contamination during surgical removal of the tissue. In contrast, all three cryopreserved cell products and thawed cells were completely free from contaminating microorganisms. This indicates that not only the process was aseptic (in that it did not introduce contamination) but our cell processing procedure actually eliminated contamination that was present before the process. Additionally, the processing space where the cell isolation, cryopreservation, and thawing took place was tested for the presence of microbial contamination: samples from both the surfaces and air in the clean room were collected, tested and found to be free of any viable microorganisms: an indication that the space remained aseptic from outside air and that nothing from the cells/tissue contaminated the working space.

In a separate set of experiments in a non-clinical-grade research environment, studies were conducted using testicular tissue from organ donors to further improve the results of cryopreservation of human testicular cells. These studies used the same enzymatic mixture.

The cell isolation and cryopreservation procedures were conducted the same except where indicated above and below.

Two key changes were made over the original protocol. First, instead of adding complete cryopreservation media to the cells before cryopreservation, the cells were resuspended in part of the cryopreservation medium—most notable the standard amount HSA and half of the standard amount PBS. The standard amounts DMSO and dextran were suspended in the other half of the standard amount of PBS and added slowly, over the course of a minute, drop-wise to the cells resuspended in the HSA/PBS. Secondly, the cells were cryopreserved according to the same controlled-rate freezing protocol except the final temperature of the protocol was lower from −120° C. to −140° C.

The two-step method of adding cryopreservation media significantly increased the number of total viable cells recovered after cryopreservation and thawing.

The altered controlled-rate freezing program significantly increased the number of total viable cells recovered after cryopreservation and thawing.

TABLE 4

Recovery of Total Viable Cells Using Altered Cryopreservation Techniques

| Patient | Modified Controlled-Rate Freezing | | | Modified Medium Addition | | | Modified Controlled-Rate Freezing and Medium Addition Combined | | |
|---|---|---|---|---|---|---|---|---|---|
| | Normal CRF Protocol | Elongated CRF Protocol | P-value | Normal Medium Addition | 2-Step Medium Addition | P-value | Normal | Elongated CRF and 2-Step Medium Addition | P-value |
| 1 | 26.8% | 31.8% | 0.0294 | ND | ND | ND | ND | ND | ND |
| 2 | ND | ND | ND | 24.0% | 28.0% | 0.041 | ND | ND | ND |
| 3 | 18.1% | 20.1% | 0.2326 | 20.1% | 22.9% | 0.0855 | 18.1% | 22.9% | 0.0106 |
| 4 | 24.3% | 25.1% | 0.33 | 25.1% | 29.1% | 0.0171 | 24.3% | 29.1% | 0.0036 |

Human testicular cells were cryopreserved either with the standard methods of cryopreservation medium addition and controlled-rate freezing or with either elongated controlled-rate freezing program and/or a 2-step cryopreservation medium addition. The number of viable cells recovered from each vial was counted and compared with the number of viable cells that had been cryopreserved in each vial. Percentages represent an average of 4 vials cryopreserved and thawed. Two sample T test was used for statistical analysis and P < 0.05 was considered as significant.
ND = Not determined.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of clinical processing and cryopreservation of a cell-containing sample, the method comprising:
   obtaining testicular tissue from an individual,
   suspending the testicular tissue, or cells obtained from the tissue, in 0.5 volume of a first cryopreservation medium comprising 10% HSA and PBS; and
   adding 0.5 volume of a second cryopreservation medium comprising PBS, 1% dextran, and 10% DMSO to the cells or tissue in the first cryopreservation medium, wherein the second cryopreservation medium is added drop wise over the course of 0.5 to 10 minutes;
   placing the cryopreservation medium containing the cells or tissue in a cryopreservation vial;
   cooling the vial to 4° C. and holding the vial at 4° C. for a period of time;
   cooling the vial at a rate of −1° C. per minute to a temperature of −80° C.;
   cooling the vial at a rate of −50° C. per minute to a temperature of −140° C.;
   holding the vial at −140° C. for a period of time between 0.1 and 60 minutes; and
   transferring the vial to the vapor phase of liquid nitrogen.

2. The method of claim 1, wherein the vial is held at 4° C. for 5-60 minutes.

3. The method of claim 2, wherein the vial is held at 4° C. for 10 minutes.

4. The method of claim 1, wherein the second cryopreservation medium is added drop wise over the course of 1 minute.

5. The method of claim 1, wherein the first cryopreservation medium and the second cryopreservation medium are added to the cells or tissue by an automated syringe.

6. The method of claim 1, wherein the cell sample cryopreserved is a dissociated cell suspension.

7. The method of claim 1, wherein the cell sample cryopreserved is at least one tissue fragment.

8. The method of claim 1, wherein the testicular tissue is from a prepubertal male.

9. A method of clinical processing of a cell-containing sample, the method comprising:
   obtaining and cryopreserving cells or tissue from an individual according to the method of claim 1; and
   thawing the cryopreserved cells or tissue in an automated thawing device.

10. The method of claim 1, further comprising optionally dissociating the tissue to form a single cell suspension.

* * * * *